BEST AVAILABLE COPY

DEFENSIVE PUBLICATION

SEARCH ROOM

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED MAY 27, 1969

862 O.G. 1011

T 862,002

794,416

TRIESTERS AND THEIR USE AS PLASTICIZERS

Lloyd P. Foster, P.O. Box 511, Kingsport, Tenn. 37662

Filed Jan. 27, 1969. Published May 27, 1969
Int. Cl. C08f *45/36;* C07c *69/66*
U.S. Cl. 260—31.6
No Drawing. 5 Pages Specification Novel triesters of the formula:

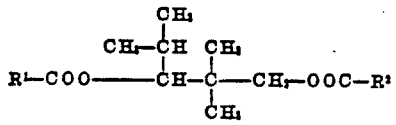

in which one of $R^1$ or $R^2$ is alkyl and the other has the formula $R^3COOCH_2$— in which $R^3$ is alkyl are useful as plasticizers for polymeric resinous materials, particularly polyvinyl chloride. The novel triesters are manufactured by reacting a glycol monoester with glycolic acid and by then reacting the resulting product with an alkanoic acid.